United States Patent [19]  [11] 4,014,747
Kenyon  [45] Mar. 29, 1977

[54] CARTRIDGE FOR A BACTERIA SCREENING DEVICE FOR CONTINUOUSLY MONITORING AND RECORDING THE EXISTENCE OF AIR BORNE BACTERIA AND OTHER MICROORGANISMS

[76] Inventor: Charles L. Kenyon, 15 MacArthur Drive, Old Greenwich, Conn. 06870

[22] Filed: Dec. 4, 1975

[21] Appl. No.: 637,832

[52] U.S. Cl. .............................. 195/127; 195/139
[51] Int. Cl.² ..................... C12B 1/02; C12K 1/04; C12K 1/06
[58] Field of Search ............ 195/127, 103.5 R, 120, 195/138; 23/253 TP, 232 R, 253 R

[56] References Cited
UNITED STATES PATENTS

| 3,128,239 | 4/1964 | Page | 195/127 |
|---|---|---|---|
| 3,129,144 | 4/1964 | Page et al. | 195/127 |
| 3,728,081 | 4/1973 | Bidanset | 23/253 R |
| 3,902,971 | 9/1975 | Fletcher et al. | 195/103.5 R |
| 3,922,203 | 11/1975 | Aldridge et al. | 195/103.5 M |

Primary Examiner—A. Louis Monacell
Assistant Examiner—Thomas G. Wiseman
Attorney, Agent, or Firm—Bryan & Bollo

[57] ABSTRACT

A cartridge for a bacteria screening device for detecting and recording the existence of bacteria and other microorganisms in a gaseous medium, such as a hospital operating room atmosphere, arranged to continuously or intermittently expose active culture media to a flow of the gaseous medium to impinge the bacteria and other microorganisms thereon and to thereafter incubate the exposed portions of the culture medium for detection and recording purposes. In the bacteria screening device, different active culture media, responsive to different bacteria, are on opposite surfaces of a strip mounted on supply and take up reels in an enclosed cartridge having apertures forming opposed limited exposure areas for the two sides of the strip. Interleaved with the strip carrying the culture media is a separating strip to prevent contact of exposed surfaces of culture media. The cartridge, designed to contain sufficient culture media for the monitored period of time, e.g., one day, is mounted in a housing which includes a drive means engageable with the take up reel to convey the strip carrying the culture medium between the supply and take up reels, an incubation oven arranged to supply heat to the strip wound upon the take up reel to incubate the bacteria and other microorganisms impinged thereon, and an inlet duct arranged to receive a flow of the gaseous medium and to direct it upon the opposed limited exposure portions of the culture media strip. The inlet duct branches into upper and lower ducts arranged to impinge the gaseous medium upon both surfaces of the strip at the same time. The ducts are arranged to flow the gaseous medium in a direction transverse to the direction of travel of the strip, and the ducts are curved adjacent the strip to centrifugally distribute the bacteria and other microorganisms according to their mass across the width of the strip.

9 Claims, 5 Drawing Figures

CARTRIDGE FOR A BACTERIA SCREENING DEVICE FOR CONTINUOUSLY MONITORING AND RECORDING THE EXISTENCE OF AIR BORNE BACTERIA AND OTHER MICROORGANISMS

CROSS REFERENCE TO RELATED APPLICATION

This application is a continuation-in-part of Ser. No. 484,993 filed July 1, 1974, now U.S. Pat. No. 5,956,070 which was a continuation-in-part of Ser. No. 246,264 filed Apr. 21, 1972, now abandoned.

BACKGROUND OF THE INVENTION

1. Field of the Invention

This invention relates to the field of detecting bacteria and other microorganisms present in a gaseous medium, generally either air in a location it is important to monitor, such as a hospital operating room, or air or another gas into which liquid particles have been injected by aerosol techniques.

Often it is desirable to continuously monitor or screen the levels of bacteria existing in a particular location or substance. Hospitals, in operating rooms and nurseries, are occasionally plagued by outbreaks of staphlococcus and other bacteria and the early detection of the existence of these microorganisms will aid in their solution. Continuous monitoring of hospital operating room, for example, would show at what time during the day hostile microorganisms became present. Correlating this information with information as to which patient was present at that time will permit the problem to be rapidly narrowed down and solved.

Additionally, it is often desirable to be able to steadily monitor liquid bacteria levels, e.g., as a check upon water pollution.

2. Description of the Prior Art

Devices and methods for monitoring or screening bacteria and other microorganisms are known. Examples of such devices and methods are found in U.S. Pat. No. 2,894,239 to Page, U.S. Pat. No. 3,127,329 to Anderson, and U.S. Pat. No. 2,894,877 to Sinden. Such devices have not been altogether satisfactory for automatically monitoring the existence of bacteria on a continuing basis in a variety of situations. The known devices, primarily being manual laboratory devices, are not convenient to use and adaptable to a wide variety of circumstances which may be encountered, and generally include complicated or cumbersome apparatus ill suited for inconspicuous placement as a monitoring device.

SUMMARY OF THE INVENTION

One of the objects of this invention is to provide a cartridge for a bacteria screening or monitoring device capable of unattended sampling of bacteria or other microorganisms carried by a gaseous medium and capable of simple recurrent use by unskilled persons without the need for careful control of sterile conditions in handling the device, and to provide a device capable of detecting a wide range of bacteria and adaptable to a wide range of monitoring conditions with a construction which is simple and inexpensive to build and reliable in operation. Another object of the invention is to provide a bacteria screening device which is more suitable for commercial production and use.

According to this invention, a cartridge is arranged so it may be mounted within the bacteria screening device and removed after it has been exposed to a gaseous or atomized liquid medium upon which bacteria screening or monitoring is desired.

Within the cartridge is a strip having wet activated culture medium on the exposed surfaces of the strip; the strip is mounted to translate from a supply to a take up reel; at least one of the wheels is constructed to engaged with and be driven by a drive means within the screening device upon insertion of the cartridge into the screening device. An exposure window is provided within the cartridge so that a limited portion of wet activated culture can be exposed to the flow of the gaseous medium upon which screening is desired to cause the inoculation of the culture. The cartridge is shaped such that the exposed culture will be in a heat transfer relationship with a heating means contained in the screening device which causes the inoculated culture to incubate within the cartridge. The cartridge is enclosed to maintain itself and its contents sterile and wet prior to insertion within the screening device.

In another aspect of the invention, the bacteria screening device for detecting and recording the existence of bacteria or other microorganisms in gaseous media comprises strip means mounted on supply and take up reels and carrying a culture medium on an exposable surface thereof, housing means for containing the strip means with culture medium thereon, inlet means in the housing for receiving a flow of the gaseous medium and directing it upon a limited portion of the strip means to impinge bacteria or other microorganisms suspended in the gaseous medium upon a limited portion of the culture medium and means for conveying the strip means between said reels to advance other limited portions of the culture medium into position for exposure to the gaseous medium. In further aspects of the invention the strip means and the supply and take up reels are mounted within a removable enclosed cartridge which is apertured to present only the limited portion of the strip means for exposure, different culture media are on the two sides of the strip means, and the cartridge contains a separating strip which is interleaved with the strip carrying the culture media to prevent exposed areas of the strip means from contacting one another. In another aspect of the invention, the housing means contains drive means connected to the take up reel for conveying the strip means either continuously or intermittently at a desired rate. In still another aspect of the invention, the inlet means in the housing branches into two ducts which impinge the gaseous flow on both sides of the strip carrying the culture medium and are arranged to direct the flow of gaseous medium in a direction transverse to the direction the strip means is conveyed, the ducts being formed with curved portions for the flowing gaseous medium to centrifugally separate and distribute microorganisms according to their mass across the width of the strip means.

Other objects, aspects and advantages of the invention will be pointed out in, or apparent from, the detailed description hereinbelow, considered together with the following drawings.

DESCRIPTION OF THE DRAWINGS

FIG. 1 is a perspective view, partially in schematic form, showing a bacteria screening device according to the present invention;

FIG. 2 is a partial section on line 2—2 of FIG. 1;

DESCRIPTION OF THE PREFERRED EMBODIMENT

Figure 1:
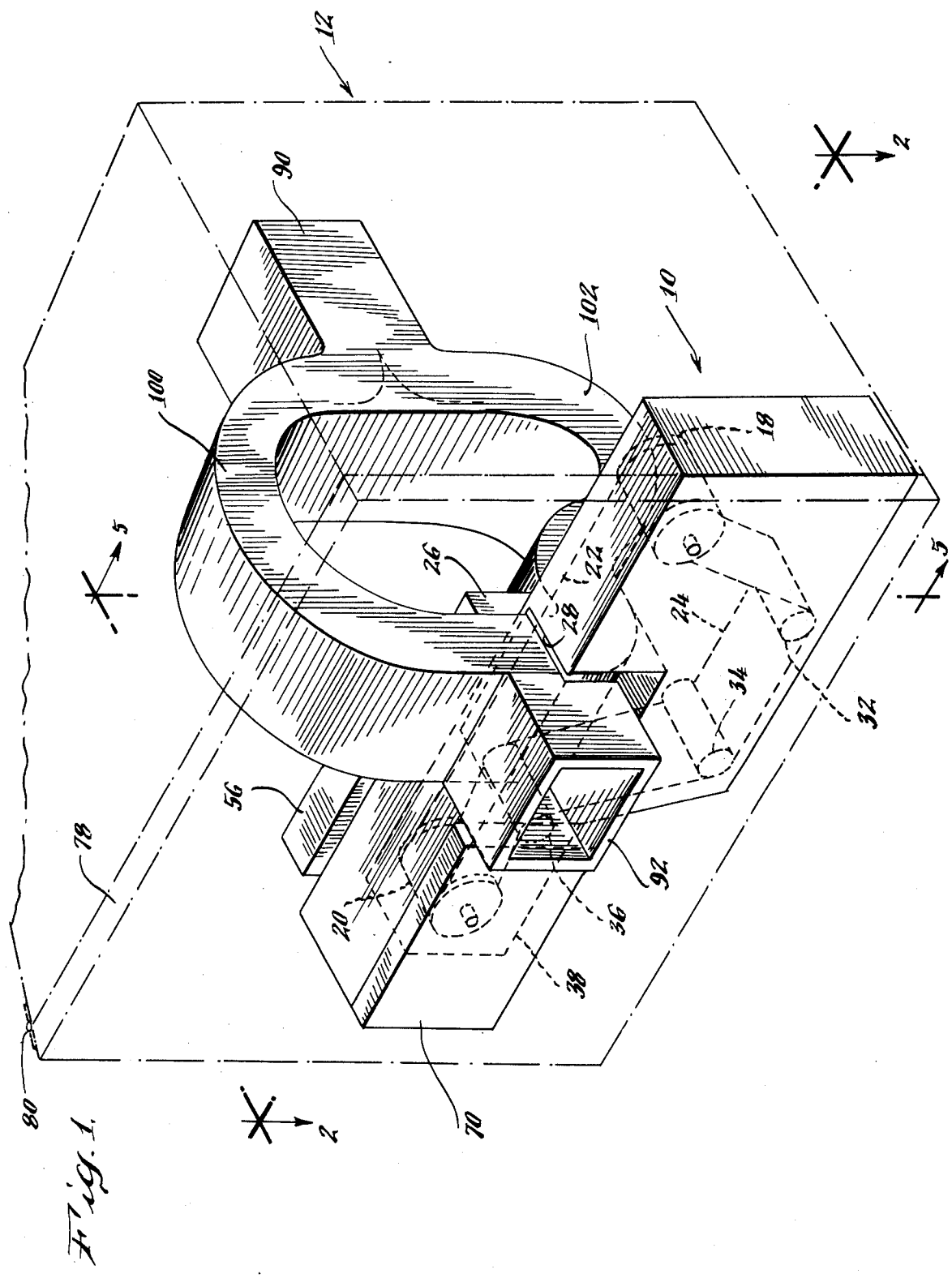

FIG. 1 illustrates a bacteria screening device 10 constructed in accordance with the present invention and arranged with an outer housing 12 designed to receive a removable and replaceable inner cartridge 14 containing culture media to be exposed to a gaseous medium containing bacteria or other microorganisms to be detected. The housing 12, shown essentially in schematic form, is supplied with the gaseous medium to be monitored and, accordingly, is either placed in the medium or is connected to the medium by means of suitable ducting.

Figure 4:
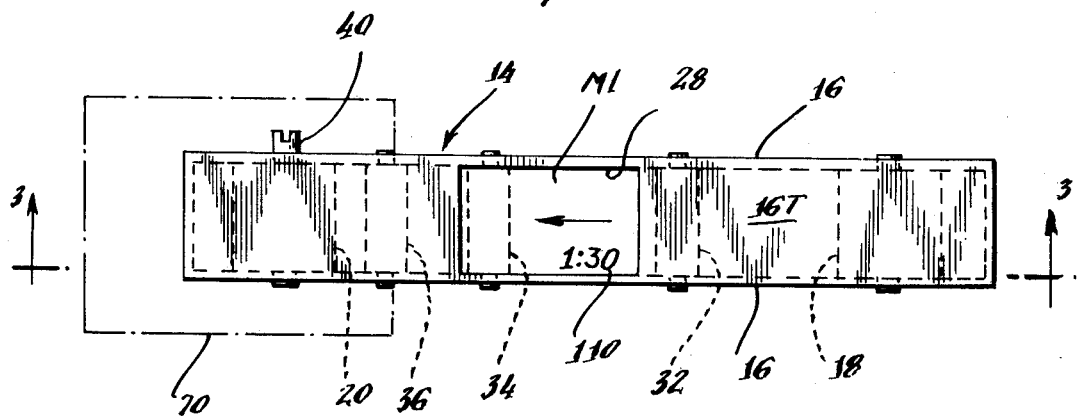
FIG. 4 is a top view of the cartridge of FIG. 3.
Figure 3:
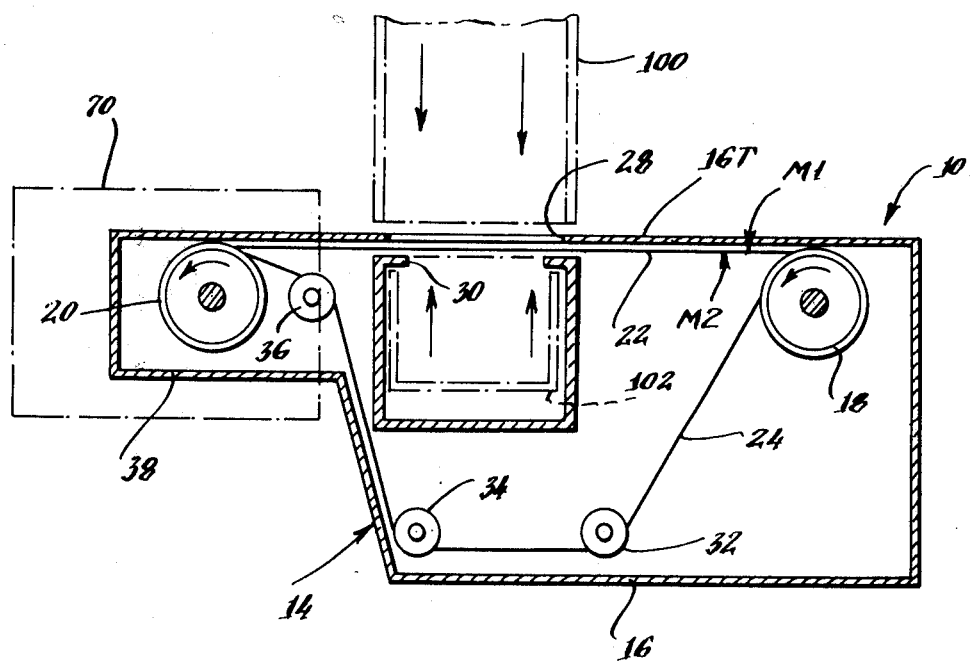
FIG. 3 is a side sectional view of a cartridge for use in the screening device of FIG. 1.

The cartridge 14, as shown for example in FIGS. 3 and 4, comprises an outer casing 16, made for example of molded plastic, which encloses a supply reel 18 and a take up reel 20. Trained over the supply and take up reels are a culture medium strip 22 and a separating strip 24. The culture medium strip, which is arranged to be exposed to the gaseous medium for detection of bacteria or other microorganisms therein, is made for example from a 25 m.m. width of cellulose acetate and has different active culture media M1 and M2 adhered to its opposite surfaces.

Different culture media respond to different microorgansims, and therefore the different culture media M1 and M2 can provide a wide range of bacterial detection, and will be selected to be of types to respond to the particular microorganisms whose detection is desired. By utilizing the appropriate media broad band screening, isolation and differentiation and other special purpose results are obtainable. For example, to detect staphlococcus, shigella, salmonella, and other microorganisms of interest in a hospital atmosphere, beef nutriment and trypticase soy agar are suitable as culture media M1 and M2. In addition, the different culture media M1 and M2 may be supplied with dyes and other materials useful in optical scanning and luminesence techniques, such as the Darkfield techniques, for counting and identifying bacterial colonies on the culture media. Separating strip 24 also is selected according to the type of bacteria to be detected. For example, for aerobic bacteria, a porous separating strip 24 will prevent sealing of exposed strip 22 during incubation and allow effective incubation and colony propagation by providing the air necessary to bacterial growth; on the other hand, anaerobic bacteria detection will be enhanced by using a nonporous and smooth separating strip 24 effectively sealing much of the inoculated media.

Furthermore, a wide cartridge strip can be used in which each side of the strip contains multiple zones which can contain different culture media and which are longitudinally separated from one another. The separation means can also be divided into zones associated with the cartridge zones. These separating zones can be either porous or nonporous depending on whether aerobic or anaerobic bacteria is to be detected.

As shown in FIG. 3, cartridge 14 is arranged so that culture medium strip 22 extends along the inside of top wall 16T of casing 16 and above a central rectangular channel 26 formed through cartridge 14 and surrounded by means of an interior casing wall 16C which joins casing side walls 16S. The strip 22 thus passes between top wall 16T and the top portion of interior wall 16C. Above channel 26, casing top wall 16T and the top portion of interior wall 16C are apertured to provide registering windows 28 and 30 which together expose limited lengthwise portions of culture medium M1 and culture medium M2 carried on opposite sides of strip 22. As will be explained in greater detail below, the strip 22 has its culture media M1 and M2 exposed to the gaseous medium through windows 28 and 30.

As shown in FIG. 3, the separating strip 24 is out of contact with the culture medium strip 22 as it is exposed, the separating strip 24 being trained over pulleys 32, 34 and 36 mounted within cartridge 14, the separating strip finally rejoining culture medium strip 22 as it is wound upon take up reel 20 to separate the exposed areas of the culture medium strip 22 from one another and to prevent contamination of one part of the culture medium by another.

Cartridge 14 is designed to supply a sufficient amount of active culture medium for exposure over the period of time to be monitored. For example, it is expected that in hospital operating room monitoring, a one day supply of culture medium will be provided in cartridge 14 so that the cartridge will be replaced each day with a new one. The cartridge casing 16 is designed to completely enclose the culture medium strip 22 with the exception of exposure through windows 28 and 30, and therefore the cartridge 14 protects the culture medium strip 22 from contamination. It is contemplated that the cartridges 14 will be prepared with active culture medium in a sterile atmosphere and will be enclosed within an outer sterile package which would be removed at the time a cartridge 14 is placed within housing 12.

It is further comtemplated that incubation of active culture media M1 and M2 will take place or at least begin while the strip 22 is on take up reel 20. Accordingly, cartridge 14 places the take up reel 20 in a narrowed cartridge end portion 38 adapted to transmit heat effectively from an incubation oven to the culture media M1 and M2 located on strip 22 wound upon take up reel 20.

As shown in FIG. 4, take up reel 20 is provided with a coupling stub shaft 40 which extends beyond casing 16 for attachment to a drive mechanism which will turn the take up reel 20 and advance the culture medium strip 22 past the exposure areas provided by windows 28 and 30.

Cartridge 14 is inserted in a space therefor in housing 12 for exposure to the gaseous medium to be monitored. Housing 12 is provided with a drive mechanism 50 having a drive shaft 52 arranged to couple with the coupling shaft 40 of cartridge 14. Drive shaft 52 is driven by an electric motor 54 operating through a gear train 56 to provide the desired rate of advance of culture medium strip 22. To provide different rates of advancement of the culture medium strip 22, gear train 56 may be made adjustable or motor speed may be made adjustable. Similarly, to provide intermittent, rather than continuous motion of strip 22, a timer switch may be used to control the application of power from an external source 60 to motor 54.

Figure 2:
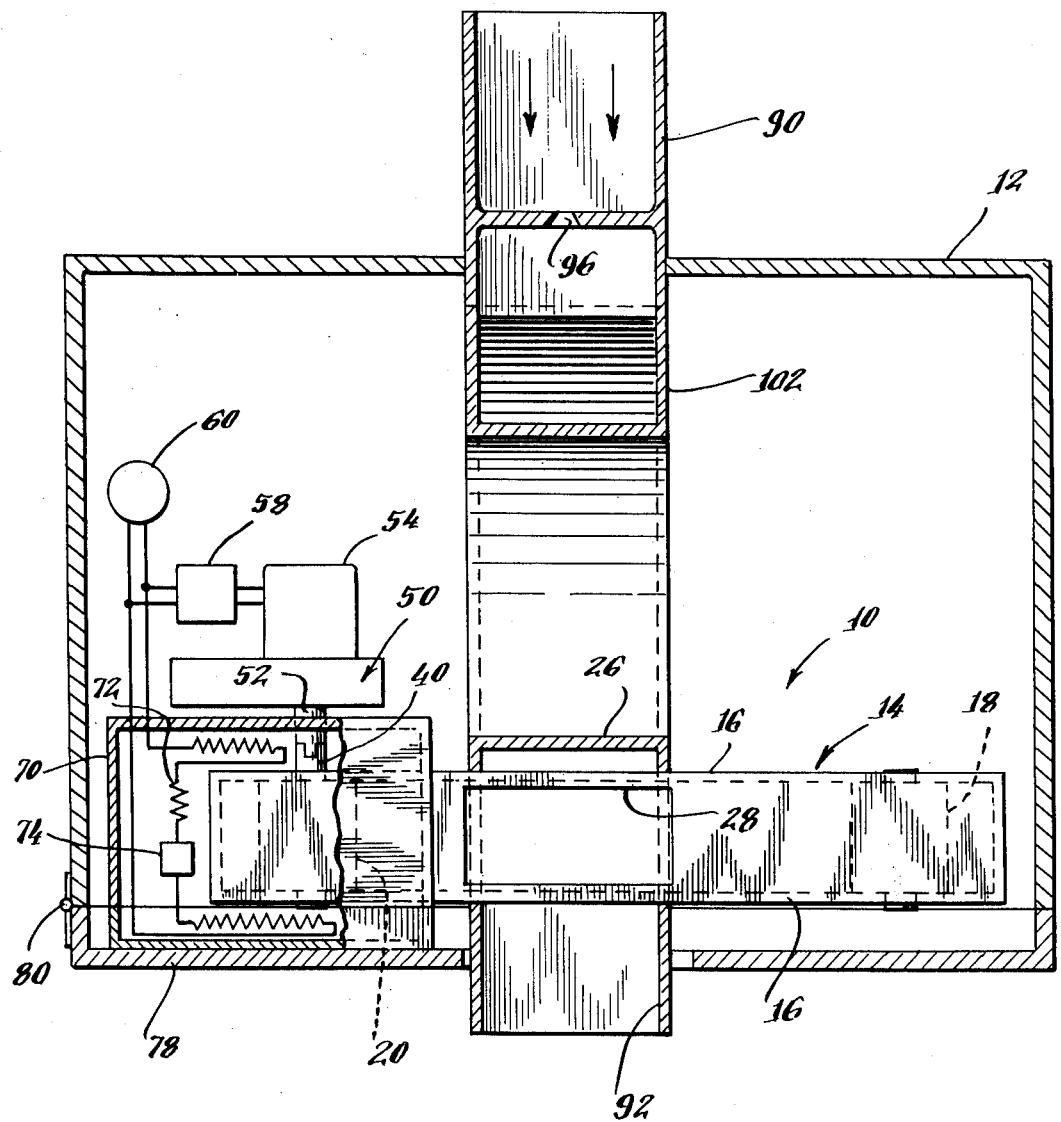

Housing 12 also contains an incubation oven 70 arranged to surround the reduced end portion 38 of cartridge 14 and to supply uniform heat, e.g., at an incubation temperature of 37° C., to take up reel 20 therein. Incubation oven 70 is formed with resistance heating elements 72 shown schematically in the drawing, and controlled by a temperature sensitive switch 74, both of which are connected in an appropriate fashion to the external source of power 60. As shown in FIG. 2, a portion 76 of the incubation oven 70 is removable to permit insertion of cartridge 14 in housing 12. Preferably the removable portion 76 of the incubation oven is formed as part of a rear door 78 for housing 12, the rear door 78 being hinged at 80 to open the housing 12 to give access to its interior for insertion and removal of cartridges 14.

Figure 5:
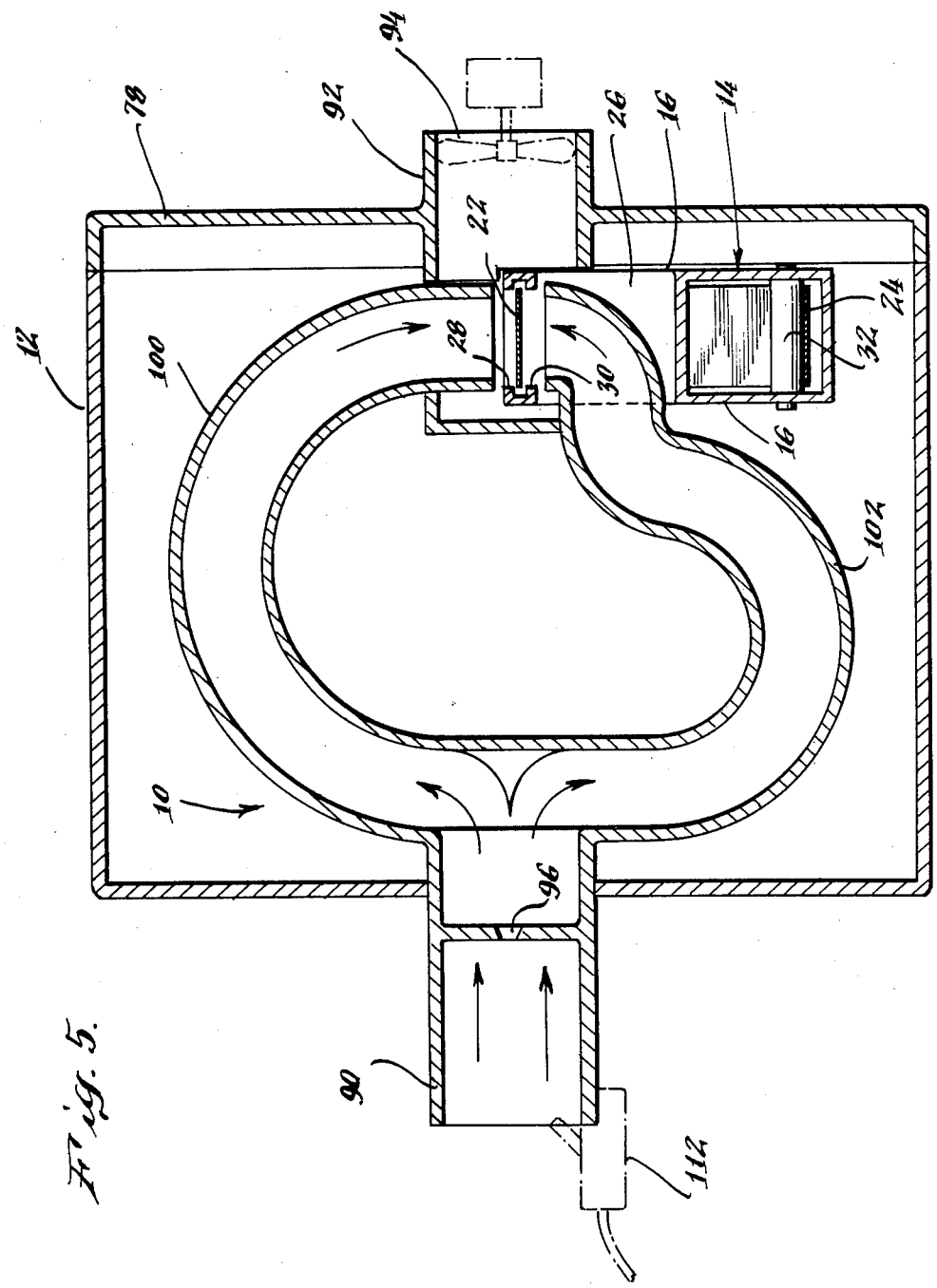
FIG. 5 is a section on line 5—5 of FIG. 1, showing the flow of gaseous medium through the device.

As shown in FIGS. 1 and 5, housing 12 is provided with an inlet duct 90 to receive a flow F of the gaseous medium to be monitored and an outlet duct 92 through which the flow F exits. The flow of gaseous medium is either externally induced, for example by mounting the bacteria screening device 10 in cooperation with an air conditioning unit to provide a flow of gaseous medium therethrough, or is induced internally by means of, e.g., the fan indicated schematically at 94 in outlet duct 92 (FIG. 5). To adjust the flow F to a desired rate depending upon the means used for inducing flow, the amount of flow F through inlet duct 90 is controlled by a variable aperture 96 therein, constructed for example in the form of an iris. As illustrated in FIGS. 1 and 5, the inlet duct 90 branches into upper and lower ducts 100 and 102 each arranged to carry one half of the flow F of gaseous medium and to direct the two branches of gaseous medium against the opposed limited portions of culture medium strip 22 exposed through windows 28 and 30, thereby to impinge bacteria or other microorganisms suspended in the gaseous medium against the exposed portions of active culture medium M1 and M2. Since the two flows are equal, and on opposite sides of strip 22, the net force on the strip 22 is negligible, and the flow does not interfere with travel of strip 22 in cartridge 14.

As shown in FIG. 5, the upper and lower ducts 100 and 102, and the outlet duct 92, are arranged to flow the gaseous medium in a direction transverse to the direction of travel of the culture medium strip 22. As further shown in FIG. 5, the upper inlet duct 100 is arranged with a curved path terminating just above the upper surface of culture medium strip 22. The lower inlet duct 102 follows a path into the channel 26 within cartridge 14 and terminates in a curved portion ending adjacent the bottom surface of culture medium strip 22. The curving regions of upper and lower ducts 100 and 102 impose a centrifugal acceleration upon the microorganisms contained in the flowing gaseous medium and accordingly cause the microorganisms to distribute themselves according to mass across the width W of the cultural medium strip 22. Therefore, for example, particles of greater mass will be located further toward the right side of strip 22 (as seen in FIG. 5) than particles of lesser mass, and a bacterial mass distribution results which aids in analyzing cultures which appear on culture medium strip 22 after incubation.

From the foregoing it can be seen that bacteria screening device 10 permits either continual or intermittent unattended monitoring of gaseous medium to detect and record microorganisms therein. The strip 22 can be time coded with indicia as shown at 110 in FIG. 4 in order to simplify correlation with other time related data. The device can be used with gaseous media as described, and can further be used to detect microorganisms in a liquid by using an atomizing or vaporizing device as shown schematically at 112 in FIG. 5 to introduce the liquid's microorganisms into the flow F.

Accordingly, the device permits bacteria and other microorganisms to be readily and easily monitored without the need for a complicated or cumbersome device, and moreover, permits active and sterile culture media to be readily supplied to the device without the need for complicated acts of replacement or sterile conditions.

Although specific embodiments of the invention have been disclosed herein in detail, it is to be understood that this is for the purpose of illustrating the invention, and should not be construed as necessarily limiting the scope of the invention, since it is apparent that many changes can be made to the disclosed structures by those skilled in the art to suit particular applications.

I claim:

1. A cartridge for removable mounting in a screening device that detects and records the existence of bacteria and other microorganisms present in a gaseous medium, said cartridge comprising:
   a. an outer casing;
   b. a supply reel and a take up reel within said casing, at least one of said reels comprising means for engaging with and being driven by means on said screening device;
   c. a strip comprising active culture medium on a surface thereof, said strip mounted to translate from said supply reel to said take up reel;
   d. an exposure window permitting contact of said gaseous medium with a limited portion of said active culture when said cartridge is mounted in said screening device;
   e. separating means for preventing contact between exposed portions of said active culture; and
   f. shaped means coacting with heating means in said screening device to permit incubation heating of exposed portions of said strip.

2. A cartridge according to claim 1, wherein both surfaces of said strip comprise active culture medium.

3. A cartridge according to claim 2, wherein each surface of said strip comprises a different active culture medium.

4. A cartridge according to claim 3, wherein one surface of said strip comprises beef nutriment and the other surface comprises trypticase soy agar.

5. A cartridge according to claim 2, wherein said separating means comprises a separating strip.

6. A cartridge according to claim 2, wherein said separating means permits exposed culture to promote the growth of aerobic bacteria.

7. A cartridge according to claim 2, wherein said separating means permits exposed culture to promote the growth of anaerobic bacteria.

8. A cartridge according to claim 2, wherein said strip is time coded.

9. A cartridge according to claim 2, wherein the active culture medium of at least one of said surfaces comprises a bioluminescent dye.

* * * * *